United States Patent [19]

Zhang

[11] Patent Number: 5,525,738
[45] Date of Patent: Jun. 11, 1996

[54] PROCESS FOR THE MANUFACTURE OF ALKYL KETENE DIMERS BY DIMERIZATION WITH TERTIARY AMINES

[75] Inventor: Jian J. Zhang, Wilmington, Del.

[73] Assignee: Hercules Incorporated, Wilmington, Del.

[21] Appl. No.: 217,590

[22] Filed: Mar. 24, 1994

Related U.S. Application Data

[63] Continuation-in-part of Ser. No. 37,203, Mar. 26, 1993, Pat. No. 5,052,997.

[30] Foreign Application Priority Data

Oct. 5, 1993 [GB] United Kingdom .................. 9309603

[51] Int. Cl.$^6$ .................................................. C07D 305/12
[52] U.S. Cl. ........................................................ 549/329
[58] Field of Search ............................................. 549/329

[56] References Cited

U.S. PATENT DOCUMENTS

| 2,238,826 | 4/1941 | Sauer | 549/329 |
|---|---|---|---|
| 2,369,914 | 2/1945 | Sauer | 549/329 |
| 2,369,919 | 2/1945 | Sauer | 260/550 |

FOREIGN PATENT DOCUMENTS

| 2335488 | 2/1975 | Germany | 549/329 |
|---|---|---|---|
| 2927118 | 10/1981 | Germany | 549/329 |
| 3434212 | 3/1986 | Germany | 549/329 |
| 748980 | 4/1994 | Germany | 549/329 |
| 264545 | 11/1988 | Japan | 549/329 |

OTHER PUBLICATIONS

Sauer, J. C., Am. Chem. Soc. 69, pp. 2444–2448 (1947).
Sauer, J. A. C. S., vol. 69, pp. 2444–2448 (1947).

*Primary Examiner*—James H. Reamer
*Attorney, Agent, or Firm*—Ivan G. Szanto; Roy V. Jackson

[57] ABSTRACT

A process is disclosed for the synthesis of alkyl ketene dimers by the dehydrohalogenation of a $C_8$–$C_{22}$ saturated or unsaturated linear fatty acid halide, comprising reacting the fatty acid chloride with a cyclic tertiary amine in a solvent that is selected from the group consisting of cycloalkanes and alkanes at a temperature of up to 75°, mechanically separating tertiary amine hydrochloride salts from alkyl ketene dimer dissolved in the solvent, and recovering the alkyl ketene dimer from the solvent.

28 Claims, No Drawings

PROCESS FOR THE MANUFACTURE OF ALKYL KETENE DIMERS BY DIMERIZATION WITH TERTIARY AMINES

This is a continuation-in-part of U.S. patent application Ser. No. 037,203 filed Mar. 26, 1993, now U.S. Pat. No. 5,052,997.

This invention relates to a process for the synthesis of alkyl ketene dimers by the dehydrohalogenation of $C_8$–$C_{22}$ saturated or unsaturated linear fatty acid chlorides with tertiary amines in an inert solvent.

BACKGROUND OF THE INVENTION

It is well known to react reaction of saturated linear fatty acid chlorides with linear tertiary amines in a variety of inert solvents to make disubstituted ethanones, such as alkyl ketene dimers, which are useful as constituents of paper sizes as well as for other applications in industry. For instance, U.S. Pat. Nos. 2,238,826 and 2,369,919, and an article by J. C. Sauer, *Ketene Dimers from Acid Halides,* in the Journal of the American Chemical Society, 69 2444–8 (1947) describe such reactions. Among the known useful solvents are benzene, toluene, xylene, ligroin, chlorobenzene, dichlorobenzene, diethyl ether, dibutyl ether, chloroform, carbon tetrachloride, and trichloroethylene. The known families of solvents can be classified as:

1. alkanes and alkane petroleum fractions;
2. cycloalkanes such as cyclohexane and methylcyclohexane;
3. aromatic hydrocarbons such as benzene, toluene, and xylene;
4. chlorinated solvents such as chlorobenzene, dichlorobenzene, chloroform, carbon tetrachloride, and trichloroethylene; and
5. ethers such as diethyl ether.

The reaction in the said solvents to produce alkyl ketene dimer (AKD) in solution also produces linear tertiary amine hydrochloride (LTEA-HCl) as a finely divided precipitate. For some of the known solvent families, problems encountered in the alkyl ketene dimerization reaction are low AKD selectivity (<80%), an excessively viscous dimerization mixture, or very small amine-hydrochloride crystals in the dimerization slurry that are hard to separate by mechanical procedures such as filtration and/or centrifugation and decantation.

U.S. Pat. Nos. 2,238,826 and 2,369,919 indicate that saturated acyclic amines free of active hydrogen are preferred for the said reaction, although they indicate that suitable amines include 1-methylpiperidine, 1-isopropylpiperidine, and 1-methylpyrrolidene. From the disclosure, of the '919 patent it is apparent that the use of the preferred linear amines requires a very dilute reaction mixture (100–200 parts solvent per tenth mol of each reactant to obtain a yield of 60 to 97%. That degree of dilution appears to be necessary to prevent the dimerization reaction slurry from becoming highly viscous, which would make separation of a linear tertiary amine hydrochloride (LTEA-HCl) precipitate from the reaction mixture extremely difficult and impossible by filtration as disclosed in the patent.

German OLS 29 27 118 discloses a process to make diketenes using of a mixture of amines, which includes trimethylamine and at least one other tertiary amine. The trimethylamine is said to avoid the high viscosity in the reaction mixtures with fatty acid halides that higher-substituted trialkylamines were found to cause. The other amine or amines may include 1-methylpiperidine or 1-methylpyrrolidene. The solvents used include alkanes and cyclo alkanes, as well as aromatic hydrocarbons, the reaction temperature is between 60° and 90° C., and the post-reaction heating is at 80°. Separation of LTEA-HCl precipitate from the dimerization slurry involves liquid/liquid water extraction of the LTEA-HCl salt, which introduces moisture that is likely to cause hydrolysis of the alkyl ketene dimer and lessening of product yield. Yields of 87 to 92% are obtained and presumably cannot be improved further because of the inherent nature of the reaction.

There is a need for an alkyl ketene dimerization process that avoids excessive viscosity and small amine-hydrochloride crystals in the dimerization slurry, to facilitate the separation of amine-hydrochloride precipitates in consistently high yields by such mechanical separation methods as filtration, sedimentation and decantation, and without using uneconomic volumes of solvent, as disclosed in U.S. Pat. No. 2,369,919.

Also, because the conventional dimerization solvents used in present industrial applications are either unacceptably toxic, particularly benzene, diethyl ether and toluene, used in the said U.S. Pat. No. 2,369,919), or are known to be environmentally objectionable, including the whole class of the chlorinated solvents. There is therefore a need for a alkyl ketene dimerization process that uses a solvent with less health and environmental problems than aromatic hydrocarbons, such as benzene and toluene or halogenated solvents as used in the German OLS.

SUMMARY OF THE INVENTION

According to the invention, a process for the synthesis of alkyl ketene dimers by reacting a $C_8$–$C_{22}$ saturated or unsaturated linear fatty acid chloride with a cyclic tertiary amine in an inert solvent at a temperature of up to 75° C., mechanically separating tertiary amine hydrochloride salts from the alkyl ketene dimer in the solvent, and recovering the alkyl ketene dimer by evaporation of the solvent, characterized in that the tertiary amine has the structure:

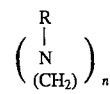

in which R represents a $C_1$–$C_7$ substituted or unsubstituted alkyl group and n is an integer from 2 to 10.

Preferably the alkyl group R contains one to three carbon atoms and n is four or five, and more preferably the tertiary amines for use in the invention are N-methylpyrrolidine, N-methylpiperidine, or N-ethylpiperidine. The most preferred cyclic tertiary amine is N-methylpyrrolidine.

The preferred solvents are cycloalkanes or alkanes, preferably containing from 5 to 10 carbon atoms. The cycloalkanes may be either unsubstituted or substituted by an alkyl group having one to four carbon atoms, and the alkanes may be either linear or branched. The more preferred solvents are cycloalkanes.

The amount of solvent used for the reaction is preferably between about 30% and 100% by mass of the solvent, based upon the mass of the fatty acid chloride or mixture of fatty acid chlorides. More preferably, the amount of solvent is just above the amount needed to avoid the saturation concentration of alkyl ketene dimer in the solvent at the reaction cycle temperatures, namely, to provide an alkyl ketene dimer concentration in the reaction slurry in the range of 1.0 molar to 3.65 molar.

DETAILED DESCRIPTION OF THE INVENTION

Among the cycloalkanes, the best results are secured by use of cyclohexane or methylcyclohexane, in particular methylcyclohexane. The preferred alkane is heptane. The most preferred combination of cyclic tertiary amine and solvent is methylpyrrolidine and methylcyclohexane In the process according to the invention, long-chain carboxylic acid halides with 12 to 22 carbon atoms, or their mixtures, are preferred. Among the halides, the chlorides are the most suitable. Suitable chlorides are conventionally derived from their corresponding carboxylic acids by chlorination with chlorinating reagents such as, phosphorus trichloride, phosphorus pentachloride, thionyl chloride, and phosgene. Furthermore, mixtures of carboxylic acid chlorides of naturally occurring fatty acids are suitable for this process, e.g., fatty acids from tallow oil and palm oil. Particular preferred is a mixture of palmitoyl chloride and stearyl chloride as the starting material.

According to the invention, the quantity of tertiary amines used is preferably a 1.00–1.15 molar ratio relative to the fatty acid chloride, more preferably a 1.10 molar ratio. A quantity of amine less than 1.00 molar relative to the fatty acid chloride can result in an incomplete reaction and poorer alkyl ketene dimer quality. On the other hand, an amine level exceeding a 1.15 molar ratio is not economically justified and may also adversely affect the quality of the alkyl ketene dimer.

It is possible to add the fatty acid chloride to the tertiary amine solution in the aliphatic hydrocarbon solvent, or to add the tertiary amine to the fatty acid chloride solution in aliphatic hydrocarbon, or simultaneously to add both fatty acid chloride and tertiary amine to the solvent. However, the preferred method is dropwise addition of the fatty acid chloride, either as is or dissolved in aliphatic hydrocarbon solvent, to a tertiary amine solution, also in aliphatic hydrocarbon solvent.

The reaction of the dehydrochlorination of fatty acid chloride by tertiary amine is exothermic. The addition of fatty acid chloride to the tertiary amine solution in aliphatic hydrocarbon solvent is preferably carried out at a temperature ranging from room temperature to 70° C., if necessary accompanied by cooling to prevent the temperature from exceeding 70° C.

In order to complete the dehydrochlorination reaction of the fatty acid chloride and the dimerization reaction of ketene monomer, the complete reaction mixture is preferably maintained at an elevated temperature of up to 70° C. for at least 30 minutes and up to 5 hours, preferably at a temperature of at least 50° C. and more preferably between 55° and 65° C. for between 2 and 3 hours. This post-reaction heat treatment generally lowers the viscosity of the reaction slurry and improves the alkyl ketene dimer quality.

As indicated above, the amount of solvent used for the reaction is preferably at least sufficient and preferably in excess of the amount necessary to maintain the alkyl ketene dimer in solution at the reaction mixture. In some circumstances it may be desired to add additional solvent during the course of the reaction to avoid the precipitation of the alkyl ketene dimer along with the tertiary amine hydrochloride salt.

For the physical separation of the tertiary amine hydrochloride crystals from the alkyl ketene dimer solution in the reaction solvent, vacuum filtration, or filtration hastened by the use of centrifugal force may be satisfactory, preferably the latter. In general, the amine-hydrohalide precipitates must have all linear dimensions greater than 2 microns to use mechanically assisted separation. Best results are secured by use of the filtration hastened by centrifugal force at a temperature from 65° C. to 75° C. to avoid the precipitation of alkyl ketene dimer.

After the physical separation of the precipitated tertiary amine hydrochloride salts, the final stage of the process is the recovery of alkyl ketene dimer by the removal of the solvent and the remaining tertiary amine. Conventional techniques for removing volatile substances from relatively non-volatile substances are appropriate, including distillation or vacuum distillation. Preferably the distillation process is performed under an inert atmosphere, and the solvent is recovered for re-use.

This invention is further disclosed by the following examples.

EXAMPLE 1

This Example shows the production of an alkyl ketene dimer using N-methylpyrrolidine in methylcyclohexane.

140 parts (by weight) of N-methylpyrrolidine in 460 parts of methylcyclohexane was placed in an oven dried 1 L 5-necked flask equipped with nitrogen inlet/outlet, PTFE paddle stirrer, condenser, and dropping funnel. 410 parts of palmitoyl chloride was then added dropwise over a period of 50 minutes with stirring, during which the temperature rose to 35°–45° C. from room temperature.

After the addition was completed, the fluid reaction mixture was heated and maintained at 60° C. for 90 minutes. The tertiary amine hydrochloride precipitate was separated from the alkyl ketene dimer solution in methylcyclohexane by suction filtration follow by wash the tertiary amine hydrochloride salt cake with 100 parts of hot (~70° C.) methylcyclohexane. The filtrate containing the alkyl ketene dimer was then stripped off the solvent and the excess N-methylpyrrolidine under reduced pressure using a rotary evaporator at 55° C. to obtain the alkyl ketene dimer. Analysis of the product showed that it contains an alkyl ketene dimer assay of 91.3% and a non-volatile content of 99.8%.

EXAMPLE 2

This Example shows the preparation of an alkyl ketene dimer using N-methylpyrrolidine in cyclohexane.

Alkyl ketene dimer was prepared using N-methylpyrrolidine in the cyclohexane dimerization solvent and following the same procedure as in Example 1, except the reaction temperature was 40° C. Analysis of the product showed that it contained an alkyl ketene dimer assay of 93.0% and a non-volatile content of 99.8%.

EXAMPLE 3

This Example shows the preparation of an alkyl ketene dimer using N-methylpiperidine in methylcyclohexane An alkyl ketene dimer was prepared using N-methylpiperidine as a base in methylcyclohexane as the dimerization solvent, and following the same reaction procedure as the Example 1. Analysis of the product showed that it contained an alkyl ketene dimer assay of 91.8% and a non-volatile content of 99.7%.

EXAMPLE 4

This Example shows the preparation of an alkyl ketene dimer using N-methylpyrrolidine in heptane.

Alkyl ketene dimer was prepared using N-methylpyrrolidine in heptane as the dimerization solvent and following the same reaction proceduue as in Example 1. Analysis of the product showed that it contained an alkyl ketene dimer assay of 87.3% and a non-volatile content of 99.8%.

I claim:

1. A process for the synthesis of alkyl ketene dimers by the dehydrohalogenation of a $C_8$–$C_{22}$ saturated or unsaturated linear fatty acid halide, or a mixture of $C_8$–$C_{22}$ linear fatty acid halides, comprising reacting the fatty acid halide with a cyclic tertiary amine in a solvent selected from the group consisting of alkanes and cycloalkanes at a temperature of up to 75° C., mechanically separating tertiary amine hydrochloride salts from alkyl ketene dimer dissolved in the solvent, and recovering the alkyl ketene dimer from the solvent, characterized in that the tertiary amine has the structure:

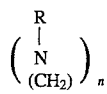

in which R represents a $C_1$–$C_7$ substituted or unsubstituted alkyl group and n is an integer from 2 to 10.

2. A process for the synthesis of alkyl ketene dimers as claimed in claim 1, in which the solvent is selected from the group consisting of cycloalkanes and alkanes containing 5 to 10 carbon atoms.

3. A process for the synthesis of alkyl ketene dimers as claimed in claim 2, in which the cycloalkanes are selected from the group consisting of unsubstituted cycloalkanes and cycloalkanes substituted by an alkyl group having one to four carbon atoms.

4. A process for the synthesis of alkyl ketene dimers as claimed in claim 2, in which the solvent is selected from the group consisting of heptane, cyclohexane, and methylcyclohexane.

5. A process for the synthesis of alkyl ketene dimers as claimed in claim 1, in which the amount of solvent is just above the amount needed to provide an alkyl ketene dimer concentration in the reaction slurry in the range of 1.0 molar to 3.65 molar.

6. A process for the synthesis of alkyl ketene dimers as claimed in claim 4, in which the amount of solvent is just above the amount needed to provide an alkyl ketene dimer concentration in the reaction slurry in the range of 1.0 molar to 3.65 molar.

7. A process for the synthesis of alkyl ketene dimers as claimed in as claimed in claim 1, in which the fatty acid halide or mixture is a linear fatty acid chloride or a mixture comprising a linear fatty acid chloride.

8. A process for the synthesis of alkyl ketene dimers as claimed in claim 7, in which the fatty acid chloride or mixture comprises a linear fatty acid chloride having 12 to 22 carbon atoms.

9. A process for the synthesis of alkyl ketene dimers as claimed in claim 1, in which the alkyl group R contains one to three carbon atoms and n is four or five.

10. A process for the synthesis of alkyl ketene dimers as claimed in claim 4, in which the alkyl group R contains one to three carbon atoms and n is four or five.

11. A process for the synthesis of alkyl ketene dimers as claimed in claim 10, in which the tertiary amine is N-methylpyrrolidine.

12. A process for the synthesis of alkyl ketene dimers as claimed in claim 10, in which the tertiary amine is N-methylpyrrolidine.

13. A process for the synthesis of alkyl ketene dimers as claimed in claim 11, in which the solvent is methylcyclohexane.

14. A process for the synthesis of alkyl ketene dimers as claimed in claim 10, in which the tertiary amine is N-piperidine.

15. A process for the synthesis of alkyl ketene dimers as claimed in claim 11, in which the solvent is cyclohexane.

16. A process for the synthesis of alkyl ketene dimers as claimed in claim 1, in which the quantity of tertiary amine used is 1.00–1.15 molar relative to the fatty acid chloride.

17. A process for the synthesis of alkyl ketene dimers as claimed in claim 15, in which the quantity of tertiary amines used is 1.10 molar relative to the fatty acid chloride.

18. A process for the synthesis of alkyl ketene dimers as claimed in claim 16, in which the quantity of tertiary amines used is 1.10 molar relative to the fatty acid chloride.

19. A process for the synthesis of alkyl ketene dimers as claimed in claim 1, in which the fatty acid chloride is added dropwise to the tertiary amine dissolved in the solvent.

20. A process for the synthesis of alkyl ketene dimers as claimed in claim 1, in which the fatty acid chloride is added to the tertiary amine at a temperature in the range of room temperature to 70° C.

21. A process for the synthesis of alkyl ketene dimers as claimed in claim 1, in which the reaction includes the step of maintaining the reaction mixture at a temperature in the range of room temperature to 70° C. for at least 30 minutes and up to 5 hours before the tertiary amine hydrochloride salts are separated.

22. A process for the synthesis of alkyl ketene dimers as claimed in claim 4, in which the reaction includes the step of maintaining the reaction mixture at a temperature in the range of room temperature to 70° C. for at least 30 minutes and up to 5 hours before the tertiary amine hydrochloride salts are separated.

23. A process for the synthesis of alkyl ketene dimers as claimed in claim 21, in which the reaction mixture is maintained at a temperature between 55° and 65° C. for between 2 and 3 hours.

24. A process for the synthesis of alkyl ketene dimers as claimed in claim 22, in which the reaction mixture is maintained at a temperature between 55° and 65° C. for between 2 and 3 hours.

25. A process for the synthesis of alkyl ketene dimers as claimed in claim 1, in which the separation of the tertiary amine hydrochloride salts includes the step of filtration.

26. A process for the synthesis of alkyl ketene dimers as claimed in claim 4, in which the separation of the tertiary amine hydrochloride salts includes the step of filtration.

27. A process for the synthesis of alkyl ketene dimers as claimed in claim 1, in which the separation of the tertiary amine hydrochloride salts includes the step of decantation after centrifugation.

28. A process for the synthesis of alkyl ketene dimers as claimed in claim 4, in which the separation of the tertiary amine hydrochloride salts includes the step of decantation after centrifugation.

* * * * *

UNITED STATES PATENT AND TRADEMARK OFFICE
CERTIFICATE OF CORRECTION

PATENT NO. : 5,525,738

DATED : June 11, 1996

INVENTOR(S) : Jian Jian Zhang

It is certified that error appears in the above-identified patent and that said Letters Patent is hereby corrected as shown below:

Column 3, line 8, insert a period -- . -- at the end of the sentence.
Column 4, line 61, insert a period -- . -- at the end of the sentence.
Column 5, lines 36-39, Claim 4 should depend on claim --3-- instead of claim "2".
Column 5, line 51, delete the repetitious phrase "as claimed in".
Column 5, beginning with line 36, claim 4 and continuing to column 6, line 63, the following claims should read as follows:

--4. A process for the synthesis of alkyl ketene dimers as claimed in claim 3, in which the solvent is selected from the group consisting of heptane, cyclohexane, and methylcyclohexane.

11. A process for the synthesis of alkyl ketene dimers as claimed in claim 7, in which the tetiary amine is selected from the group consisting of N-methylpyrrolidine, N-methylpiperidine, and N-ethylpiperidine.

12. A process for the synthesis of alkyl ketene dimers as claimed in claim 11, in which the tertiary amine is N-methylpyrrolidine.

13. A process for the synthesis of alkyl ketene dimers as claimed in claim 12, in which the solvent is methylcyclohexane.

UNITED STATES PATENT AND TRADEMARK OFFICE
CERTIFICATE OF CORRECTION

PATENT NO. : 5,525,738

DATED : June 11, 196

INVENTOR(S) : Jian Jian Zhang

It is certified that error appears in the above-identified patent and that said Letters Patent is hereby corrected as shown below:

15. A process for the synthesis of alkyl ketene dimers as claimed in claim 12, in which the solvent is cyclohexane.

17. A process for the synthesis of alkyl ketene dimers as claimed in claim 16, in which the quantity of tertiary amines used 1.10 molar relative to the fatty acid chloride.

18. A process for the synthesis of alkyl ketene dimers as claimed in claim 1, in which the fatty acid chloride is added dropwise to the tertiary amine dissolved in the solvent.

19. A process for the synthesis of alkyl ketene dimers as claimed in claim 1, in which the fatty acid chloride is added to the tertiary amine at a temperature in the range of room temperature to 70°C.

20. A process for the synthesis of alkyl ketene dimers as claimed in claim 1, in which the reaction includes the step of maintaining the reaction mixture at a temperature in the range of room temperature to 70°C for at least 30 minutes and up to 5 hours before the tertiary amine hydrochloride salts are separated.

UNITED STATES PATENT AND TRADEMARK OFFICE
CERTIFICATE OF CORRECTION

PATENT NO. : 5,525,738

DATED : June 11, 1996

INVENTOR(S) : Jian Jian Zhang

It is certified that error appears in the above-identified patent and that said Letters Patent is hereby corrected as shown below:

21. A process for the synthesis of alkyl ketene dimers as claimed in claim 4, in which the reaction includes the step of maintaining the reaction mixture at a temperature in the range of room temperature to 70°C for at least 30 minutes and up to 5 hours before the tertiary amine hydrochloride salts are separated.

22. A process for the synthesis of alkyl ketene dimers as claimed in claim 20, in which the reaction mixture is maintained at a temperature between 55 and 65°C for between 2 and 3 hours.

23. A process for the synthesis of alkyl ketene dimers as claimed in claim 21, in which the reaction mixture is maintained at a temperature between 55 and 65°C for between 2 and 3 hours.

24. A process for the synthesis of alkyl ketene dimers as claimed in claim 1, in which the spearation of the tertiary amine hydrochloride salts includes the step of filtration.

25. A process for the synthesis of alkyl ketene dimers as claimed in claim 4, in which the spearation of the tertiary amine hydrochloride salts includes the step of filtration.

UNITED STATES PATENT AND TRADEMARK OFFICE
CERTIFICATE OF CORRECTION

PATENT NO. : 5,525,783

DATED : June 11, 1996

INVENTOR(S) : Jian Jian Zhang

Page 4 of 4

It is certified that error appears in the above-identified patent and that said Letters Patent is hereby corrected as shown below:

26. A process for the synthesis of alkyl ketene dimers as claimed in claim 1, in which the separation of the tertiary amine hydrochloride salts includes the step of decantation after centerifugation.

27. A process for the synthesis of alkyl ketene dimers as claimed in claim 4, in which the separation of the tertiary amine hydrochloride salts includes the step of decantation after centrifugation.

On the title page, after the Abstract "28 Claims, No Drawings" should read --27 Claims, No Drawings--.

Signed and Sealed this

Twenty-ninth Day of April, 1997

Attest:

BRUCE LEHMAN

Attesting Officer

Commissioner of Patents and Trademarks